(12) United States Patent
Foguet et al.

(10) Patent No.: US 6,881,845 B2
(45) Date of Patent: Apr. 19, 2005

(54) PROCESS FOR PREPARING (±)TRANS-4-P-FLUOROPHENYL-3-HYDROXYMETHYL-1-METHYLPIPERIDINE

(75) Inventors: Rafael Foguet, Barcelona (ES); Jorge Ramentol, Barcelona (ES); Diego Fernandez-Cano, Barcelona (ES); Miguel P. Armengol, Barcelona (ES); Inés Petschen, Barcelona (ES); Juan Sallares, Sant Cugat (ES); Francesc X. Camps, Barcelona (ES); Manuel M. Raga, Barcelona (ES); Josep M. Castello, Barcelona (ES)

(73) Assignee: Ferrer Internacional, S.A., Barcelona (ES)

( * ) Notice: Subject to any disclaimer, the term of this patent is extended or adjusted under 35 U.S.C. 154(b) by 0 days.

(21) Appl. No.: 10/250,519

(22) PCT Filed: Jan. 4, 2001

(86) PCT No.: PCT/EP01/00049

§ 371 (c)(1),
(2), (4) Date: Sep. 15, 2003

(87) PCT Pub. No.: WO02/053537

PCT Pub. Date: Jul. 11, 2002

(65) Prior Publication Data

US 2004/0215020 A1 Oct. 28, 2004

(51) Int. Cl.$^7$ .................... C07D 211/20; C07D 211/40
(52) U.S. Cl. .................. 546/236; 546/216; 546/239; 546/289; 546/301; 546/302; 546/315; 546/322; 546/339; 560/8; 560/174; 562/405

(58) Field of Search ................. 546/216, 236, 546/239, 289, 301, 302, 315, 322, 339; 560/8, 174; 562/405

(56) References Cited

U.S. PATENT DOCUMENTS

3,912,743 A * 10/1975 Christensen et al. ........ 546/197
4,902,801 A    2/1990 Faruk et al. ................ 546/197

FOREIGN PATENT DOCUMENTS

| EP | 374674 | * | 6/1990 |
| EP | 0 812 827 A | | 12/1997 |
| WO | WO 96/36636 A | | 11/1996 |
| WO | WO 98/53824 A | | 12/1998 |
| WO | WO 00/26187 A | | 5/2000 |

OTHER PUBLICATIONS

Foguet et al. "Novel process for . . . " CA 137:78863 (2002).*
RN 103–67–3 CAS registry.*
RN 403–42–9 CAS reistry.*
Pathak et al. "Studies in fluorinated . . . " CA 94:102967 (1981).*
Stuetz, Anton et al. J. Med. Chem. (1986), 29(1), 112–25.

* cited by examiner

*Primary Examiner*—Celia Chang
(74) *Attorney, Agent, or Firm*—Birch, Stewart, Kolasch & Birch, LLP

(57) ABSTRACT

The present invention relates to a process for preparing (±)-trans-4-p-fluorophenyl-3-hyroxymethyl-1-methylpiperdine of formula (I). The present invention also relates to novel intermediates of the formula (IX) and (IX') methods for preparing said intermediates and the use of said compounds for preparing Paroxetine and Omiloxetine.

20 Claims, No Drawings

PROCESS FOR PREPARING (±)TRANS-4-P-FLUOROPHENYL-3-HYDROXYMETHYL-1-METHYLPIPERIDINE

This application is the national phase under 35 U.S.C. §371 of PCT International Application No. PCT/EP01/00049 which has an International filing date of Jan. 4, 2001, which designated the United States of America.

The present invention relates to a process for preparing (±)-trans-4-p-fluorophenyl-3-hydroxymethyl-1-methylpiperidine of formula I:

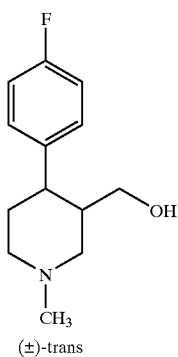

(±)-trans

The compound of formula I is a key precursor in the synthesis of (−)-trans-4-p-fluorophenyl-3-(3′,4′-methylenedioxy phenoxymethyl)-piperidine, a compound also known as paroxetine (WHO—INN), of formula II, as well as (−)-trans-N-p-flourobenzoylmethyl-4-(p-fluorophenyl)-3-(3′,4′-methylenedioxy-phenoxymethyl)-piperdine, a compound also known as omiloxetine (WHO—INN), of formula III. These compounds inhibit 5-hydroxytryptamine (5-HT) reuptake and are useful as antidepressants.

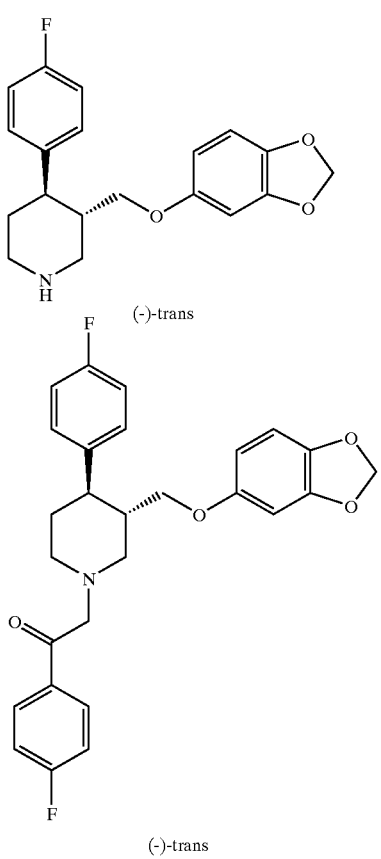

U.S. Pat. No. 3,912,743 describes for the first time the compounds of general formula A:

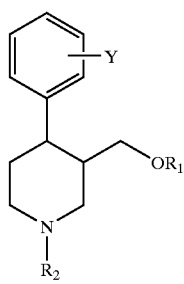

wherein, among others, Y is halogen, $R_1$ is an optionally substituted phenyl group and $R_2$ is hydrogen or alkyl. The preparation of compound A disclosed in U.S. Pat. No. 3,912,743 and subsequently in U.S. Pat. No. 4,007,196 is based on a Grignard reaction in which arecoline and 4-flourophenylmagnesium bromide are reacted. This procedure has the disadvantage that arecoline is a very irritant and expensive product. Moreover, the 1,4-addition of the Grignard reagent competes with the 1,2-addition. This leads to product mixtures and thus involves complex purification steps and results in low reaction yields. Furthermore, the immediate precursor of compound A is obtained as a mixture of cis-form and trans-form isomers. All of this hinders the industrial application of the procedure.

U.S. Pat. No. 4,902,801 discloses the preparation of compounds of general formula A by reducing 4-aryl-2,6-dioxo-3-piperidincarboxylic acid esters of general formula B:

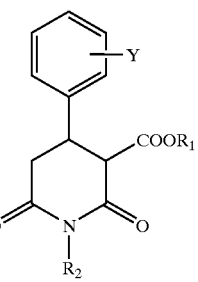

wherein, among others, Y is halogen, $R_1$ is alkyl and $R_2$ is alkyl. Compound B with Y=p-F and $R_2$=Me would lead to intermediate I. This intermediate can be synthesized by reaction of N-methyl amidomalonic acid esters with cinnamic acid esters. Cinnamic acid esters are formed only in low yields and thus the resulting process is very expensive. Other patents describe the production of intermediate B by addition of malonic acid esters to methylcyanamide (EP 374,675). According to this variant, free methylamine has to be used and, consequently, special equipment is needed. All of this leads to high manufacturing costs of both variants.

Compound I can also be prepared by reducing trans-4-flouropenyl-6-oxopiperidin-3-carboxylic acid esters (compound C), wherein $R_1$ is alkyl (EP 802,185, ES 96/00, 369, EP 812,827 and WO 98/53,824) and subsequent N-methylation (EP 802,185) or by methylation of compound C and subsequent reduction (WO 98/53,824).

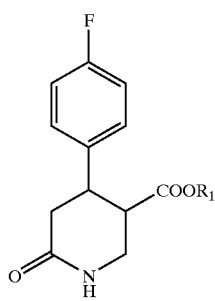

C

Compound C is prepared by adding cyanoacetic acid ester to cinnamic acid ester in the presence of a base followed by reduction and simultaneous cyclization of the resulting 2-cyano-3-arylglutaric derivative. If the reduction of the nitrile is carried out by hydrogenation, elevated hydrogen pressures may be needed (EP 812,827), which involves evident risk of defluoration or the use of platinum oxide as a catalyst, which increases the synthesis costs. The reductive cyclization (EP 802,185, EP 812,827, WO 98/53,824) generally yields cis-trans mixtures. Consequently, the undesired cis compound has to be separated by fractional crystallization or employment of a further isomerization step.

Similarly, compound D, wherein $R_1$ is alkyl, may also be a precursor of intermediate I (CA 131: 184870 and WO 00/26,187).

D

Also in the synthesis of this compound, vigorous conditions are needed for the reduction of the nitrile group.

In another method intermediate I is prepared by reducing 1-methyl-4-(4-fluorophenyl)-1,2,3,6-tetrahydropiperidine. The formation of this compound involves a reaction between methylamine, formaldehyde and α-stirene (U.S. Pat. No. 4,007,196 and WO 96/36,636). The difficulty of working with methylamine and above all the neurotoxicity of 4-aryl-1-alkyl-1,4,5,6-tetrahydropiperidine derivatives make this procedure unsafe and industrially non-applicable.

According to the background of this invention, it is desirable to provide an alternative method for the production of intermediate I, wherein said compound is preferably obtained as trans isomer directly. This would better meet the requirements for the costs, safety and ecology of the production of pharmaceutically active substances, such as paroxetine or omiloxetine.

The process of the present invention for preparing (±)-trans-4-p-fluorophenyl-3-hydroxymethyl-1-methylpiperidine is illustrated in the following reaction scheme:

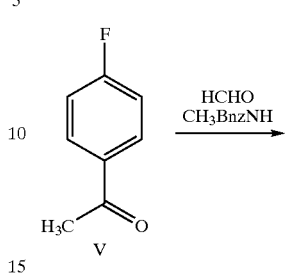

V

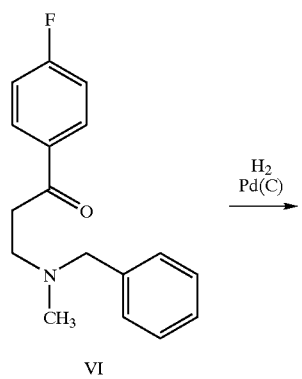

VI

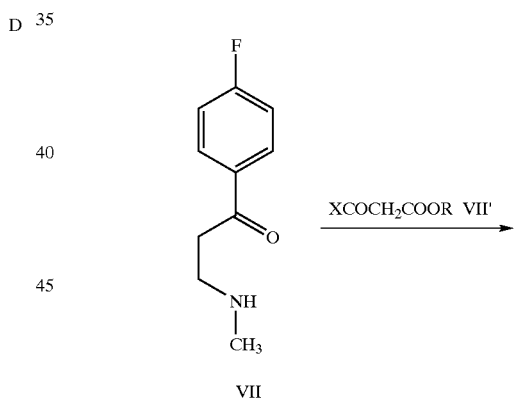

VII

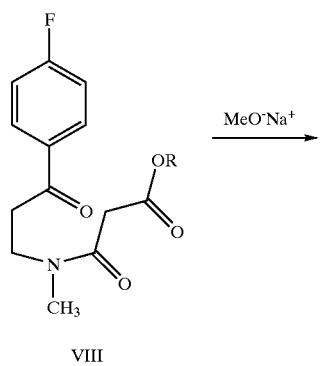

VIII

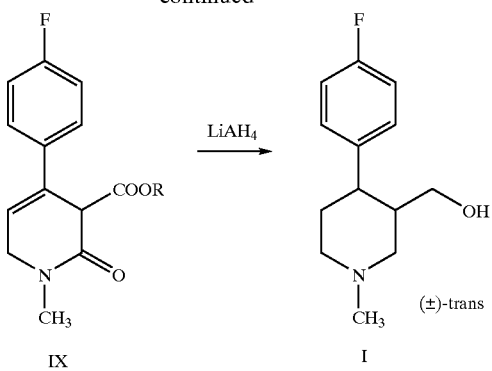

In a first step p-fluoroacetophenone V, a commercially available product, is condensed with a unit of formaldehyde (paraformaldehyde or aqueous formaldehyde) and a unit of methylbenzylamine through Mannich reaction. The reaction is generally carried out in a polar solvent (alcoholic or aqueous). The methylbenzylamine can be employed in form of its addition salts with strong inorganic or organic acids. Examples of suitable physiologically tolerated organic and inorganic acids are hydrochloric acid, hydrobromic acid, phosphoric acid, sulfuric acid, oxalic acid, maleic acid, fumaric acid, lactic acid, tartaric acid, adipic acid or benzoic acid. Other acids which can be used are described in *Fortschritte der Arzneimittelforschung,* volume 10, pages 224 et seq., Birkhäuser Verlag, Basle and Stuttgart, 1966. If the methylbenzylamine is used in form of a salt, eg. as hydrochloride, then compound VI is also isolated as a salt, eg. the hydrochloride, which has the form of a white crystalline solid.

In a second step the benzyl group is unprotected from amine VI. The removal of the benzyl group is preferably carried out with a reducing agent that essentially does neither lead to a defluorination of the fluorophenyl group nor a reduction of the carbonyl group. Suitable reducing agents comprise hydrogen in the presence of a homogeneous or heterogeneous catalyst, preferably Raney nickel or palladium on carbon (Pd/C).

Further, the removal of the benzyl group is preferably carried out in a medium containing water or at least one alcohol or a mixture comprising at least one alcohol and water. The latter medium is the most appropriate to achieve a better conversion and to minimize the reduction of the carbonyl group of compound VI to an alcohol group. If an alcoholic reaction medium or a medium containing at least one alcohol is employed, the alcohol is preferably selected from $C_1$–$C_4$-alcanols, eg. methanol, ethanol, n-propanol, isopropanol, n-butanol, and mixtures thereof. Particular preference is given to mixtures of water and methanol. In this manner, reductions may be accomplished at an earlier stage with outstanding yield and purity.

It is convenient to isolate compound VII in the form of an addition salt as defined above, eg. as hydrochloride and liberate it in situ in the following reaction step, wherein compound VII is reacted with an alkyl 3-halo-3-oxopropionate (VII'). If compound VII is employed in form of an addition salt then the reaction with compound VII' affords two base equivalents, one for liberating the amine from the starting salt, eg. the hydrochloride, and the other for neutralizing the formed HCl. In compound VII' alkyl preferably is $C_1$–$C_4$-alkyl, especially methyl. 3-halo preferably is 3-chloro. It is not advisable that the basic medium is aqueous because then the acid chloride VII' might be hydrolyzed. Preferably, the reaction medium comprises at least one organic solvent selected from aromatic hydrocarbons, eg. benzene, toluene and xylene, chlorohydrocarbons, eg. $CH_2Cl_2$, $CHCl_3$, $CCl_4$, $C_2H_4Cl_2$, and mixtures thereof. The employed base is preferably selected from tertiary amines, eg. triethyl amine.

The intramolecular Knoevenagel condensation of compound VIII is thermodynamically favoured because a highly conjugated cyclic compound is formed.

It has been found that in a basic medium containing nitrogenous bases (pyridine, piperidine and the like), the reaction does not occur with an appropriate yield. A convenient conversion is accomplished in the presence of ammonium acetate-acetic acid or in a basic medium comprising an alkoxide. Compound IX easily crystallizes from such a reaction medium and may be isolated with high purity and yield.

Depending on the reaction conditions compound IX or a mixture with its positional isomer IX' is obtained

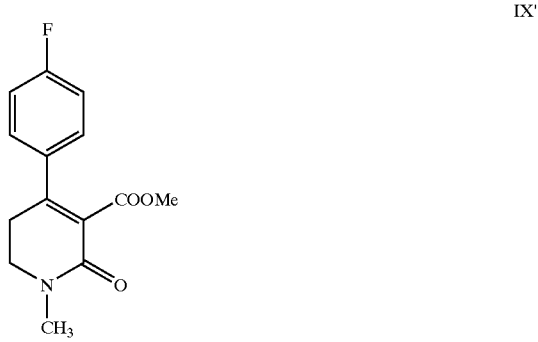

It is an object of the present invention to provide new compounds VI, VII and VIII as well as methods for preparing said compounds. The invention also embraces the acid addition salts of the compounds of formulae VI and VII with inorganic or organic acids. It is also an object of the present invention to provide new compounds IX and IX' in the form of the pure isomers or mixed in any proportion.

Finally, compounds IX and IX' may be reduced by using different hydrides, such as sodium hydride, potassium hydride, magnesium hydride, calcium hydride, sodium boron hydride, potassium boron hydride, lithium boron hydride, lithium aluminium hydride, sodium aluminium hydride, aluminium hydride, sodium hydride and bis(2-methoxyethoxy)aluminium, aluminium hydride mono($C_{1-4}$ alkoxy)aluminium, lithium aluminium di($C_{1-4}$ alkoxy) aluminium, sodium hydride and diethylaluminium or the mixtures of any of them. Particularly advantageous is lithium aluminium hydride in the presence or in the absence of an inorganic salt. The reduction may be accomplished using a borane or diborane as well. The reaction may be carried out in different low-polarity solvents, such as tetrahydrofuran (THF), ethyl ether, tert-butylmethyl ether, mixtures of toluene or an alkane, in particular a $C_6$–$C_9$-alkane (heptane, octane and the like) or a cycloalkane, in particular a $C_5$–$C_8$-cycloalkane (cyclohexane, cycloheptane and the like) and THF and the like, THF being preferred.

The process of the present invention has the advantage over processes of the prior art that three functional groups are simultaneously reduced in a single reaction step and the reduced agent is obtained only in the trans form.

Consequently, in this manner, and in contrast to most known processes, further epimerization steps are avoided.

According to a preferred embodiment, the invention is directed to a process for preparing (±)-trans-4-p- fluorophenyl-3-hydroxymethyl-1-methylpiperidine of formula

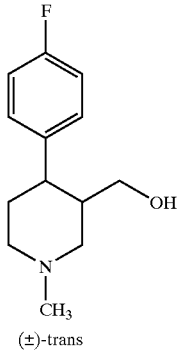

(±)-trans comprising
i) reacting p-fluoroacetophenone with formaldehyde and methylbenzylamine or an addition salt thereof with at least one inorganic or organic acid to obtain a compound of formula VI

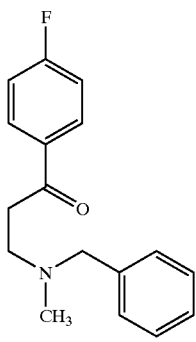

or an addition salt thereof with at least one inorganic or organic acid,
ii) hydrogenating of the compound of formula VI or the addition salt thereof to obtain a compound of the formula VII

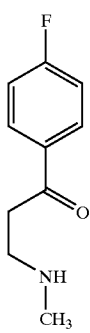

or an addition salt thereof,
iii) reacting the compound of formula VII or the addition salt thereof with an alkyl 3-halo-3-oxopropionate of the general formula VII'

XCOCH$_2$COOR     VII' wherein X is halogen, in particular chlorine or bromine, and R is an alkyl group having 1 to 4 carbon atoms to obtain a compound of formula VIII,

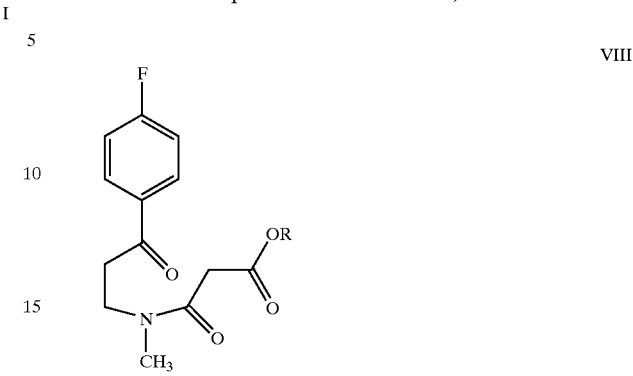

wherein R is defined as above,
iv) performing an intramolecular condensation of the compound of formula VIII to obtain a compound of formula IX or IX'

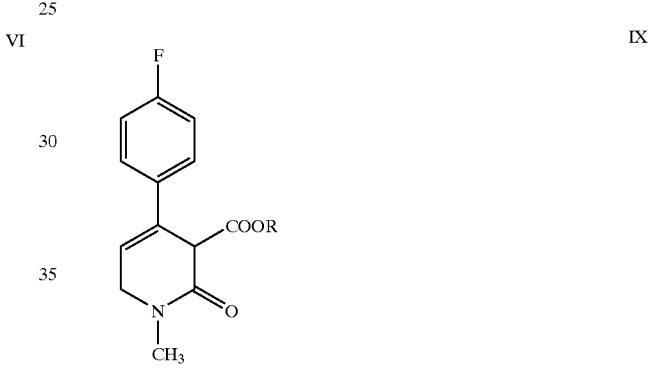

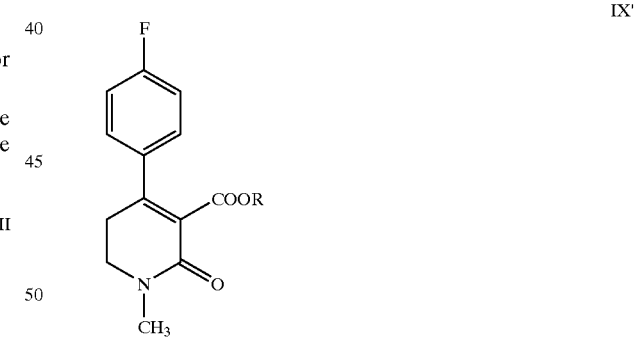

wherein R is an alkyl group having 1 to 4 carbon atoms, or a mixture thereof, and
v) reducing the compound(s) IX and/or IX' to obtain the compound of formula I.

Further embodiments of the invention refer to processes for preparing compounds of the formula I, characterised by one of the following sequences of the above reaction steps: ii) to v); iii) to v); and iv) to v). Compound I is a key precursor in the synthesis of paroxetine and omiloxetine. U.S. Pat. No. 4,902,801 describes how the racemic mixture ((±)-trans) may be resolved into the enantiomer (−)-trans of formula IV using (−)-di-p-toluoyltartaric acid.

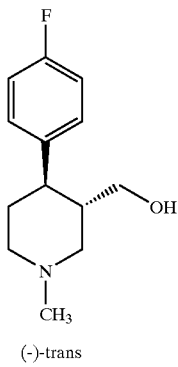

IV (-)-trans

U.S. Pat. No. 4,007,196 provides a process for the preparation of paroxetine acetate from (−)-trans-4-p-fluorophenyl-3-hydroxymethyl-1-methyl piperidine of formula IV. Spanish Patent 2,117,557 provides a process for the preparation of omiloxetine from paroxetine acetate.

The present invention is further illustrated by the subsequent non-limiting examples.

EXAMPLE 1

3-(benzyl-methylamino)-1-(p-fluorophenyl)-propan-1-one hydrochloride (VI)

A mixture of 114.12 g (0.724 mole) of benzylmethylamine hydrochloride, 21.74 g (0.724 mole) of paraformaldehyde, 100 g of p-fluoroacetophenone (0.724 mole) and 7.5 mL of concentrated HCl in 100 mL of ethanol was refluxed for 2 hours. Following the addition of another portion of paraformaldehyde (21.74 g, 0.724 mole), the mixture was refluxed for further 2 hours. 75 mL of acetone were added, stirred at 0° C. for 1 hour and the solid formed was filtered and washed with acetone. The solid (187.6 g, 84%) was pure enough to be used in the following step without prior purification.

M.p.=164–165° C.

IR (KBr), cm$^{-1}$: 3436, 3062, 2895, 2629, 2550, 1682, 1599, 1508, 1370, 1236, 741, 699.

$^1$H NMR (CDCl$_3$), δ (ppm): 8.03 m, 2H, aromatic; 7.64 m, 2H, aromatic; 7.46 m, 3H, aromatic; 7.14 m, 2H, aromatic; 4.42–4.08 m, 2H, COC$\underline{H}_2$; 3.83 q, J=7.2 Hz, 2H, C$\underline{H}_2$Ph; 3.68–3.33 m, 2H, C$\underline{H}_2$N; 2.70 s, 3H, C$\underline{H}_3$.

$^{13}$C NMR (CD$_3$OD), δ (ppm): 196.2 $\underline{C}$O; 167.2 d, J=253.1 Hz, $\underline{C}$ar-F; 133.7 d, J=2.3 Hz, $\underline{C}$ar in para position to F; 132.14 $\underline{C}$Har benzyl in ortho position; 132.13 d, J=10.3 Hz, $\underline{C}$Har in meta position to F; 131.0 $\underline{C}$Har benzyl in para position; 130.7 $\underline{C}$ar benzyl; 130.2 $\underline{C}$Har benzyl in meta position; 116.6 d, J=22.9 Hz, $\underline{C}$Har in ortho position to F; 61.4 $\underline{C}$H$_2$Ph; 52.2 $\underline{C}$H$_2$N; 40.6 $\underline{C}$H$_3$; 34.2 CO$\underline{C}$H$_2$.

EXAMPLE 2

1-(p-fluorophenyl)-3-methylamino-propan-1-one hydrochloride (VII)

To a solution of 42.15 g (0.137 mole) of compound VI dissolved in 221 mL of a MeOH-water (1:1) mixture were added 9.68 g of Pd over 5% carbon (56.5% water). The mixture was hydrogenated at atmospheric pressure for 1 hour. The catalyst was filtered and the solvent was evaporated to dryness. The solid formed was recrystallized from AcCN and acetone to give 28.6 g (96%) of compound VII as a white crystalline solid.

M.p.=153–154° C.

IR (KBr), cm$^{-1}$: 3435, 2960, 2770, 2464, 1677, 1690, 1599, 1229, 1160, 984, 854, 791.

$^1$H NMR (CD$_3$OD), δ (ppm): 8.17–8.07 sc, 2H, aromatic in meta position to F; 7.20–7.31 sc, 2H, aromatic in ortho to F; 3.60 t, J=6.0 Hz, 2H, COC$\underline{H}_2$; 3.46 t, J=6.0 Hz, 2H, C$\underline{H}_2$N; 2.82 s, 3H, C$\underline{H}_3$;

$^{13}$CRMN (CD$_3$OD), δ (ppm): 196.8 $\underline{C}$O; 167.1 d, J=254.2 Hz, $\underline{C}$ar-F; 133.7 d, J=3.4 Hz, $\underline{C}$ar in para position to F; 132.0 d, J=9.1 Hz, $\underline{C}$Har in meta position to F; 116.6 d, J=21.8 Hz, $\underline{C}$Har in ortho position to F; 45.5 $\underline{C}$H$_2$N; 35.3 CO$\underline{C}$H$_2$; 34.1 $\underline{C}$H$_3$.

EXAMPLE 3

N-[3-(p-fluorophenyl)-3-oxo-propyl]-N-methyl-malonamic acid, methyl ester (VIII, R:CH$_3$)

46.25 g (0.212 mole) of compound VII were dissolved in 370 mL of CH$_2$Cl$_2$ and 62.2 mL of Et$_3$N (45.16 g, 0.446 mole) were added under nitrogen atmosphere. The mixture was taken to 0° C. and 25.85 mL (32.9 g, 0.241 mole) of methyl 3-chloro-3-oxopropionate were added for 30 minutes. After stirring at 0° C. for further 30 minutes 70 mL of water were added. The organic layer was decanted. The aqueous layer was extracted with CH$_2$Cl$_2$ (2×100 mL). The combined organic layers were washed with water and the solvent was evaporated in vacuo to dryness to yield 60.4 g of a solid which was recrystallized from MeOH, giving 52.3 g (88%) of pure compound VIII.

M.p.=80–82° C. IR (KBr), cm$^{-1}$: 3473, 3068, 3016, 2965, 2920, 1746, 1679, 1641, 1601, 1509, 1456, 1433, 1412, 1325, 1252, 1100, 1025, 845, 785.

$^1$H NMR (CDCl$_3$), δ (ppm): Mixture of 2 isomers; 8.06–7.95 sc, 2H, aromatic in meta position to F; 7.21–7.08 sc, 2H, aromatic in ortho position to F; 3.82–3.70 sc, 5H, COOC$\underline{H}_3$+COC$\underline{H}_2$; 3.64+3.46 s+s, 2H, COC$\underline{H}_2$CO; 3.29+3.30 t, J=6.6 Hz+t, J=6.6 Hz, 2H, C$\underline{H}_2$N; 3.11+2.98 s+s, 3H, C$\underline{H}_3$.

$^{13}$C NMR (CDCl$_3$), δ (ppm): Mixture of 2 isomers; 196.9+195.3 2$\underline{C}$O in para position to F; 167.8+167.5+167.2+167.0+165.8+165.6+163.8+; 163.7 2d, $\underline{C}$ar-F+2N $\underline{C}$O+2$\underline{C}$OOCH$_3$; 132.6+132.4 d, J=3.3 Hz+d, J=3.3 Hz, $\underline{C}$ar in para position to F; 130.4+130.3 d, J=9.9 Hz+d, J=9.9 Hz, $\underline{C}$Har in meta position to F115.6+115.4 d, J=22.0 Hz+d, J=22.0 Hz, $\underline{C}$Har in ortho position to F; 52.2 COO$\underline{C}$H$_3$; 41.2+40.6 $\underline{C}$H$_2$COOCH$_3$; 45.3+44.6 $\underline{C}$H$_2$N; 37.2+33.2 N—CH$_3$; 36.5+36.3 CO$\underline{C}$H$_2$.

EXAMPLE 4

4-(p-fluorophenyl)-1-methyl-2-oxo-1,2,3,6-tetrahydropiridine-3-carboxylic acid, methyl ester (IX, R:CH$_3$)

To a solution of 50.0 g (0.178 mole) of compound VIII in 90 mL of MeOH were added 37.4 mL of 21% MeONa (0.133 mole) for 45 minutes at room temperature. After stirring for further 2 hours at room temperature, the mixture was taken to 0° C. and 7.6 mL of glacial AcOH were added. The solid formed was filtered and washed with MeOH, giving 38.7 g (82%) of a white solid pure enough to be used without prior purification.

M.p.=143–145° C.

IR (KBr), cm$^{-1}$: 3465, 3076, 3006, 2956, 2837, 1746, 1676, 1638, 1510, 1225, 1272, 1026, 843, 805.

¹H NMR (CDCl₃), δ (ppm): 7.44–7.34 sc, 2H, aromatic in meta position to F; 6.98–7.08 sc, 2H, aromatic in ortho position to F; 6.20 dd, J=3.0 Hz, J'=4.3 Hz, 1H, CH̲=C; 4.48 t, J=3.0 Hz, 1H, CH̲COOCH₃; 4.28 dt, J=18.6 Hz, J'=3.0 Hz, 1H, CH̲ₐH_bN; 4.02 ddd, J=18.6 Hz, J'=4.2 Hz, J"=3.0 Hz, 1H, CH̲ₐH̲_bN; 3.64 s, 3H, COOCH̲₃; 3.09 s, 3H, NCH̲₃.

¹³C NMR (CDCl₃), δ (ppm): 168.7 C̲OOCH₃; 162.1 d, J=247.2 Hz, C̲ar-F; 163.2 NC̲O; 132.9 C̲ar in para position to F; 131.7 CH=C̲; 126.9 d, J=7.7 Hz, C̲Har in meta position to F; 119.5 C̲H=C; 115.2 d, J=20.8 Hz, C̲Har in ortho position to F; 52.7 COOC̲H₃; 51.8 C̲HCOOCH₃; 50.5 C̲H₂; 34.1 N—C̲H₃.

EXAMPLE 5

Mixture of 4-(p-fluorophenyl)-1-methyl-2-oxo-1,2,3,6-tetrahydropiridine-3-carboxilic acid, methyl ester (IX, R: CH₃) and 4-(p-fluorophenyl)-1-methyl-2-oxo-1,2,5,6-tetrahydropiridine-3-carboxilic acid, methyl ester (IX', R:CH₃)

To a solution of 10.3 g (0.037 mole) of compound VIII in 10 mL of MeOH were added 10.4 mL of 21% MeONa (0.037 mole) for 1 hour at room temperature. After stirring for further 1 hour 2.3 mL of glacial AcOH were added. The mixture was stirred for 1.5 hours at room temperature and the solvent was removed under reduced pressure. 20 mL of CH₂Cl₂ and 20 mL of water were added. The mixture was decanted and the aqueous layer was extracted with CH₂Cl₂. The combined organic layers were washed with water and dried over. Na₂SO₄. The mixture was filtered and the solvent was removed under reduced pressure, giving 8.73 g (90%) of a solid consisting of a 1:1 mixture of compounds IX and IX'.

EXAMPLE 6

(±)-trans-4-p-fluorophenyl-3-hydroxymethyl-1-methylpiperidine (I)

To a stirred and cooled (0° C.) suspension of 2.12 g of lithium aluminium hydride in 30 mL of anhydrous THF under nitrogen atmosphere, 2.047 g (0.078 mole) of compound IX dissolved in 15 mL of anhydrous THF were added. The mixture was heated at reflux for 3.5 hours and then taken to 0° C. Successively, 2.12 mL of water, 2.12 mL of 5N NaOH and 6.36 mL of water were slowly added. The precipitate was stirred for 1 hour at room temperature, filtered and washed with THF. The filtrate was dried over Na₂SO₄ and filtered and the solvent was removed under reduced pressure, yielding an oil which was crystallized with heptane. After filtering and washing with heptane, the solid formed was recrystallized from heptane, to give 1.13 g (65%) of compound I.

M.p.=122–124° C.

IR (KBr), cm⁻¹: 3170, 2937, 2794, 1603, 151, 1466, 1223, 1064, 831, 791.

¹H NMR (CDCl₃), δ (ppm): 7.18–7.08 sc, 2H, aromatic in meta position to F; 7.01–6.90 sc, 2H, aromatic in ortho to F; 4.10 sa, 1H, OH̲; 3.66 dd, J=10.5 Hz, J'=3.0 Hz, 1H; 3.22 m, 1H; 3.10 dd, J=10.5 Hz, J=7.8 Hz, 1H; 2.89 m, 1H; 2.26 s, 3H, NCH̲₃; 2.26–2.18 m, 1H; 2.06–1.66 sc, 5H;

¹³C NMR (CDCl₃), δ (ppm): 161.1 d, J=242.8 Hz, C̲ar-F; 139.6 d, J=3.2 Hz, C̲Har in meta position to F; 115.1 d, J=20.9, C̲Har in ortho position to F; 63.1 C̲H₂OH; 59.5 C̲H₂; 56.0 C̲H₂; 46.3 C̲H₃; 44.3 C̲H; 43.6 C̲H; 34.2 C̲H₂CH₂N.

What is claimed is:

1. A process for preparing (±)-trans-4-p-fluorophenyl-3-hydroxymethyl-1-methylpiperidine of formula I

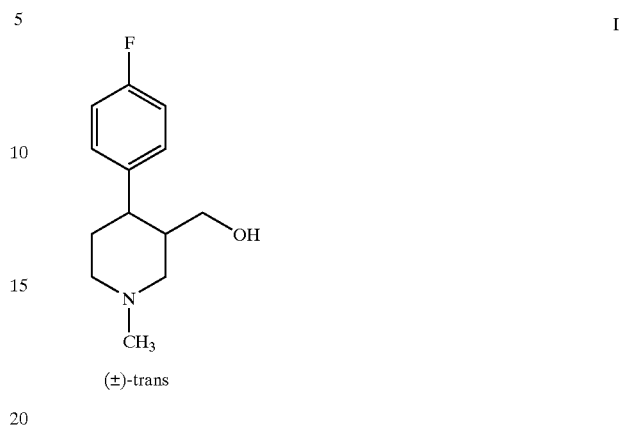

which process comprises the reduction of a compound of the formula IX or IX' or a mixture thereof

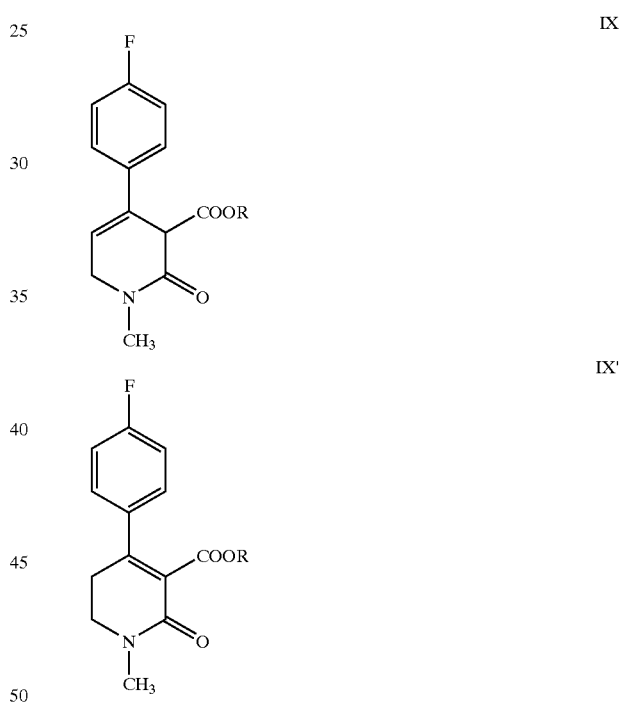

wherein R is an alky) group having 1 to 4 carbon atoms.

2. The process as claimed in claim 1, wherein the reduction is performed with a hydride or borane in a low-polarity solvent.

3. The process as claimed in claim 2, wherein the hydride is lithium aluminium hydride.

4. The process as claimed in claim 2, wherein the low-polarity solvent is selected from tetrahydrofuran, ethyl ether, tert.-butyl methyl ether and mixtures thereof, and mixtures of at least one of the aforementioned solvents with toluene and/or an alkane and/or a cycloalkane.

5. The process as claimed in claim 4, wherein the low-polarity solvent is tetrahydrofuran.

6. A compound of formula IX or IX'

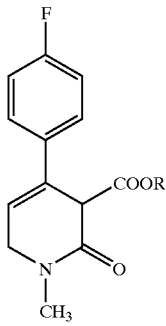

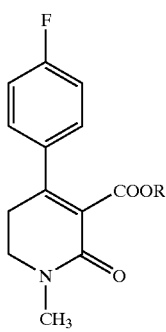

wherein R is an alkyl group having 1 to 4 carbon atoms.

7. A process for preparing a compound of formula IX or IX' or a mixture thereof,

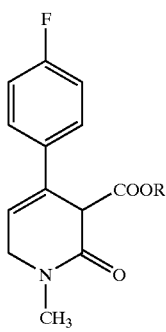

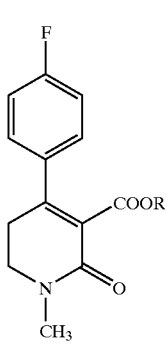

wherein R is an alkyl group having 1 to 4 carbon atoms, which process comprises the intramolecular condensation of a compound of formula VIII

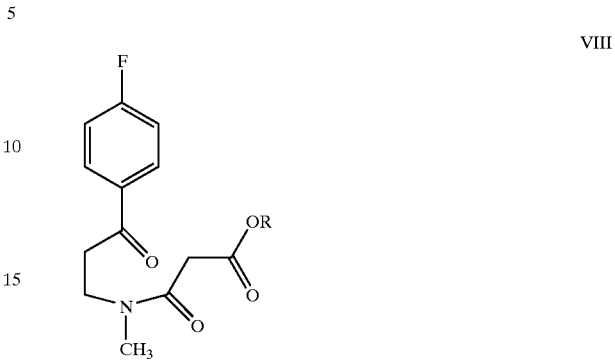

wherein R is an alkyl group having 1 to 4 carbon atoms.

8. A compound of formula VIII

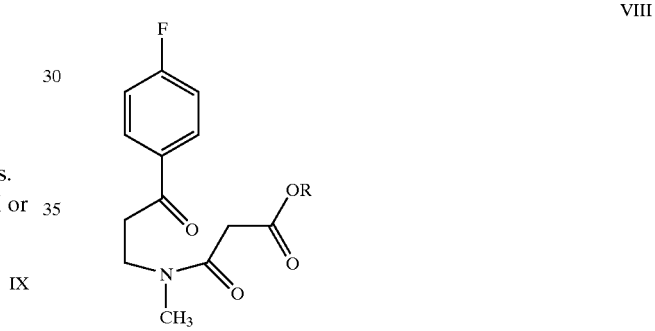

wherein R is an alkyl group having 1 to 4 carbon atoms.

9. A process for preparing compound of formula VIII

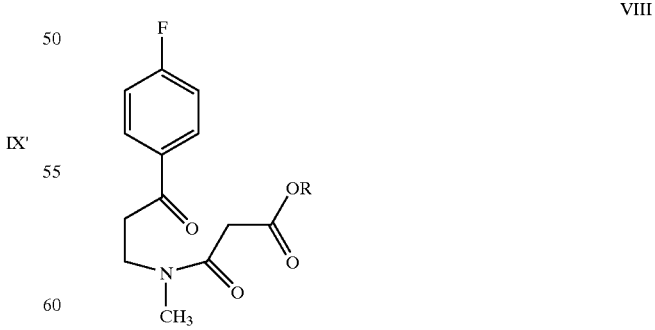

wherein R is an alkyl group having 1 to 4 carbon atoms, which process comprises the reaction of a compound of the formula VII

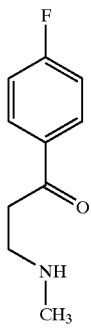

or an inorganic or organic acid addition salt thereof with an alkyl 3-halo-3-oxopropionate of formula VII'

XCOCH$_2$COOR  VII' wherein X is chlorine or bromine and R is an alkyl group having 1 to 4 carbon atoms.

10. A compound of formula VII

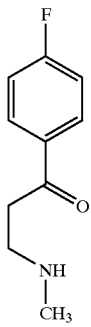

or an inorganic or organic acid addition salt thereof.

11. The compound according to claim 10, wherein the inorganic acid addition salt is the hydrochloride.

12. A process for preparing a compound of formula VII

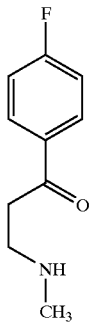

or an inorganic or organic acid addition salt thereof, wherein the inorganic acid addition salt is the hydrochloride which process comprises the hydrogenation of a compound of the formula VI

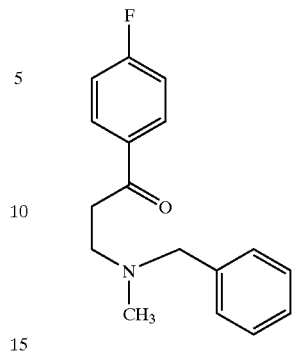

or of an addition salt thereof with an inorganic or organic acid in a polar solvent.

13. The process according to claim 12, wherein the polar solvent is selected from alkanols having 1 to 4 carbon atoms, water and mixtures thereof.

14. The process according to claim 13, wherein the polar solvent is a mixture of an alkanol having 1 to 4 carbon atoms and water.

15. A compound of formula VI

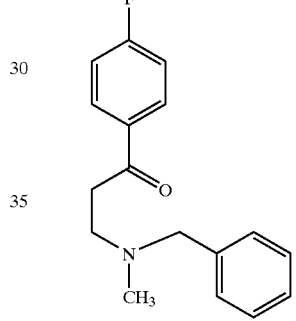

or an inorganic or organic acid addition salt thereof.

16. The compound according to claim 15, wherein the acid addition salts is the hydrochloride.

17. A process for preparing (±)-trans-4-p-fluorophenyl-3-hydroxymethyl-1-methylpiperidine of formula I

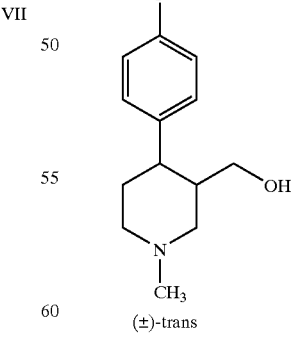

which process comprises
    i) reacting p-fluoroacetophenone with formaldehyde and methylbenzylamine or an addition salt thereof with at least one inorganic or organic acid to obtain a compound of formula VI

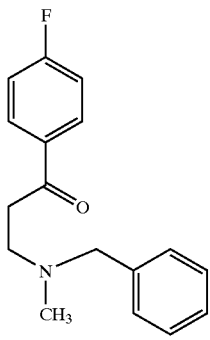

VI or an addition salt thereof with at least one inorganic or organic acid, ii) hydrogenating the compound of formula VI or the addition salt thereof to obtain a compound of the formula VII

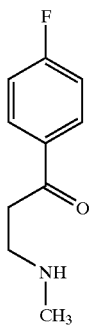

VII or an addition salt thereof, iii) reacting the compound of formula VII or the addition salt thereof with an alkyl 3-halo-3-oxopropionate of formula VII'

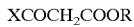 XCOCH₂COOR    VII' wherein X is chlorine or bromine and R is an alkyl group having 1 to 4 carbon atoms to obtain a compound of formula VIII,

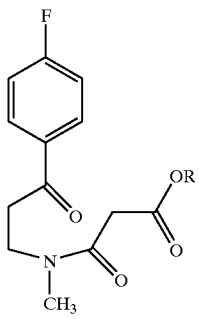

VIII wherein R is defined as above, iv) performing an intramolecular condensation of the compound of formula VIII to obtain a compound of formula IX or IX'

IX

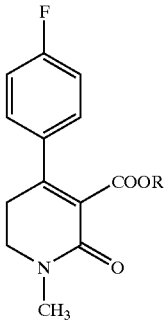

IX' wherein R is as defined above, or a mixture thereof, and v) reducing the compound(s) IX and/or IX' to obtain the compound of formula I.

18. The compound of claim 6, wherein the compound is formula IX.

19. The compound of claim 6, wherein the compound is formula IX'.

20. A composition comprising a mixture of compounds of formula IX and IX'

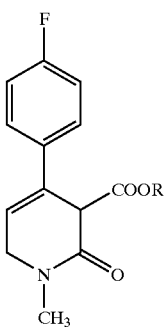

IX

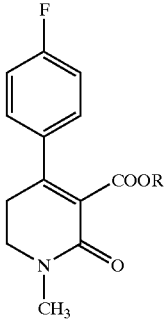

IX' wherein R is an alkyl group having 1 to 4 carbon atoms.

* * * * *